United States Patent [19]

Owens

[11] Patent Number: 4,800,867
[45] Date of Patent: Jan. 31, 1989

[54] FOOT COMFORTER

[76] Inventor: Robert Owens, R.D.#1, Box 237-A, Oakdale, Pa. 15071

[21] Appl. No.: 871,195

[22] Filed: Jun. 5, 1986

Related U.S. Application Data

[63] Continuation-in-part of Ser. No. 624,525, Jun. 25, 1984, abandoned.

[51] Int. Cl.$^4$ ............................ A61F 7/00; A43B 7/02
[52] U.S. Cl. ........................................ 126/204; 36/2.6; 128/382; 128/402
[58] Field of Search .................. 126/204; 36/2.6, 3 B, 36/3 R; 128/382, 383, 399, 400, 402, 403

[56] References Cited

U.S. PATENT DOCUMENTS

| | | | |
|---|---|---|---|
| 912,527 | 2/1909 | Batter . | |
| 1,134,389 | 4/1915 | Lack | 36/3 B |
| 1,199,914 | 10/1916 | Mossor . | |
| 1,991,601 | 11/1932 | Lasaux | 128/144 |
| 2,052,857 | 9/1936 | Widdis | 126/204 |
| 2,680,918 | 6/1954 | Behner | 36/2.6 |
| 3,000,616 | 9/1961 | Spangler | 257/12 |
| 3,050,875 | 8/1962 | Robbins | 36/3 B |
| 3,180,039 | 4/1965 | Burns, Jr. | 36/3 B |
| 3,712,288 | 1/1973 | Weiss | 126/206 |
| 3,973,336 | 8/1976 | Ahn | 36/3 B |
| 4,180,922 | 1/1980 | Cieslak et al. | 36/2.6 |
| 4,281,418 | 8/1981 | Cieslak et al. | 2/160 |
| 4,334,519 | 6/1982 | Cieslak et al. | 126/204 |

Primary Examiner—Randall L. Green
Attorney, Agent, or Firm—Arnold B. Silverman

[57] ABSTRACT

A foot comforter apparatus is adapted to ventilate, and/or may cool or heat the foot. The comforter may have a heat exchanger and has a hollow foot supporting chamber provided with an upper wall and a lower wall. The foot supporting chamber is at least partially compressible to permit cyclic application of foot pressure to cause pumping action of the fluid. Conduit means connect the heat exchanger with the pump. The conduit means is connected to the chamber at preselected positions in order to facilitate one direction flow of the fluid along and parallel to the longitudinal axis of the chamber. Spacers may be provided within the chamber to resiliently and quickly urge the upper wall away from the lower wall. Check valves may be provided in the conduits to resist undesired multi-directional flow of the fluid. One preferred embodiment of the system represents a closed circuit with heat exchanger conduit sections connecting the supply and return conduits and such conduits are charged with air. Another preferred embodiment represents an open circuit in which ambient air is drawn into the system and discharged around a user's foot.

28 Claims, 3 Drawing Sheets

FOOT COMFORTER

CROSS REFERENCE TO RELATED APPLICATION

This application is a continuation-in-part of U.S. application Ser. No. 06/624,525, filed June 25, 1984, abandoned.

BACKGROUND OF THE INVENTION

1. Field of the Invention

The present invention relates to apparatus for ventilating, cooling or warming feet and, more specifically, it relates to such apparatus which has a unique pump for circulation of air and may have heating or cooling means.

2. Description of the Prior Art

In cold environments, such as that produced by winter weather, one of the most frequent sources of discomfort results from an individual's feet becoming cold. Similarly, in hot environments discomfort due to heat may be a problem.

Various means of heating hands or feet, through the use of an article of apparel which contains a source of heat and some means for creating a pumping action to circulate a warmed fluid, have been known. See, for example, U.S. Pat. Nos. 912,527; 1,199,914; 2,052,857; 2,680,918; and 3,712,288.

U.S. Pat. No. 3,000,616 discloses a rather complex system of conduits adapted to permit heat to be taken from one section of the body and by means of pumping action said to be provided in a foot portion of the assembly causing the air to circulate to warm other portions of the body. The conduits extend along a major portion of the user's body and may tend to limit freedom of movement.

It has also been suggested in U.S. Pat. Nos. 4,180,922; 4,281,418 and 4,334,519 to provide a conduit which runs from a heat exchanger through a boot area with flow adapted to be effected by means of a manually compressible pump which appears to be disposed between the individual's ankle and knee thereby creating awkwardness in respect of ease of access to the pump.

In spite of these prior systems, there remains a very real and substantial need for an effective means of ventilating, cooling or warming and individual's feet which means is adapted to be used in an unburdensome manner.

SUMMARY OF THE INVENTION

The present invention has met the above-described need by providing a foot comforter which has a chamber adapted to function both as a means for transferring heat to or from the foot and as a pumping means. Also, the invention may provide for the ventilation of the foot without heat transfer. In addition, the system may provide for heat exchanger means and connecting conduit means. Spacer means, which are preferably resiliently compressible, are provided to facilitate efficient operation of the pump. Connections between the chamber and the supply and return conduits are such as to maximize flow from one end of the chamber's longitudinal axis to the other.

It is an object of the present invention to provide an efficient and easy to use system for ventilating, cooling or warming an individual's feet.

It is a further object of the invention to provide such a system wherein efficient integrally created pumping means are employed.

It is a further object of the present invention to provide such a system which will resist interference with normal functioning of the individual.

It is another object of the invention to provide such a system which is economical to manufacture and use.

These and other objects of the invention will be more fully understood from the following description of the invention on reference to the illustrations appended hereto.

DESCRIPTION OF THE PREFERRED EMBODIMENTS

Figure 1:
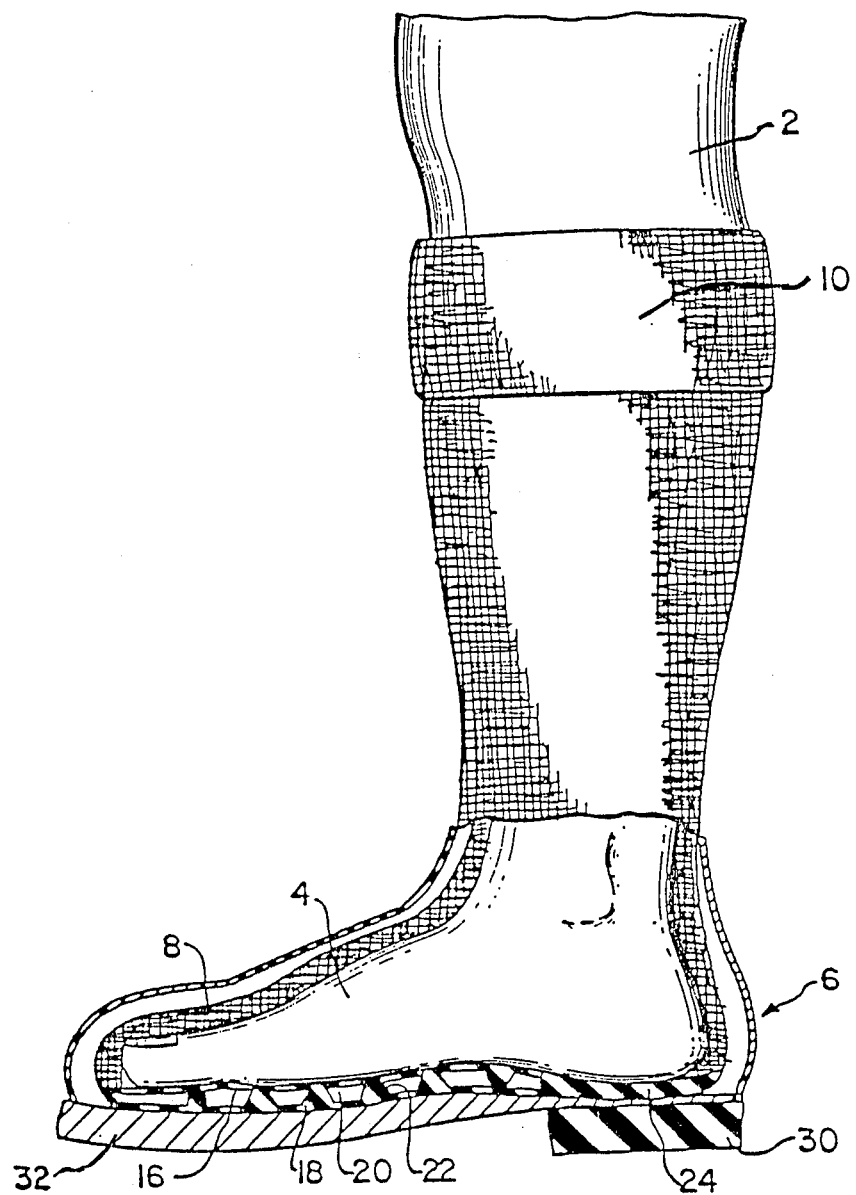
FIG. 1 is a partially broken away schematic elevational view of form of one side of the foot comforter apparatus of the present invention.

Referring to FIG. 1, there is shown a leg 2 having foot 4 disposed within boot 6. In this form of the invention, the foot comforter apparatus takes the form of a uniquely configured sock-like member. It will be appreciated, however, that the apparatus may be provided as an integral part of the shoe, boot or other article of footwear and need not be provided in a sock-like member which is adapted to be received within a further article of footwear.

For convenience of reference herein, use of the word "forward" and words of similar import, shall be intended to refer to a direction toward the toe portion of the foot 4 and use of the word "rearward" and words of similar import shall be intended to refer to a direction toward the heel portion of the foot 4.

Sock 8 may be made from any suitable fabric and will have the unique sole construction to be described hereinafter. In the form shown, toward the upper extremity, a heat exchanger 10 is provided. Heat exchanger 10 may most advantageously be thermally insulated and be disposed on the outer surface of the leg such that the two heat exchangers 10 employed with the two legs will be on opposite sides facing generally outwardly as distinguished from being positioned on the leg interior where opportunity for undesired relative contact might be presented.

As the specific type of heat exchanger may take any of a number of shapes and forms no part of the invention per se, details will not be provided. In general, it is contemplated that air will be cycled through the heat exchanger in a return direction from the foot to have its temperature elevated or reduced and then be delivered to the foot. As to sources of heat or cooling, the heat exchanger may be of any conventional variety.

Among the preferred sources of heat is to provide a resistance heating coil energized by battery means such that air passing through the heat exchanger will be heated electrically. An acceptable alternate would be to use chemical heaters such as those frequently employed by hunters and others wherein separately packaged materials are admixed to produce an exothermic reaction. In use of the apparatus to effect cooling, a frozen material, such as ice or dry ice, may be placed in the heat exchanger. It is preferred that the heat exchanger 10 have an exterior wall which is thermally insulated so as to minimize heat loss to or from the environment and body of the user.

Referring to FIG. 1 there is shown, immediately underlying the foot 4, an upper wall 16 and a lower wall 18 which cooperate to define a chamber 20. In the form illustrated, a plurality of resiliently compressible spacer members 22 which are illustrated as being generally conical in shape serve to urge the walls 16, 18 away from each other. It is preferable that spacer members 22 be comprised of a material which is generally easily compressible by the weight of a lighter than average person, but which also is capable of very rapidly urging walls 16 and 18 apart when a person's weight is removed. Under known theories of fluid mechanics, by quickly moving walls 16 and 18 to their maximum separation when a person's weight is removed, generally maximum circulation is achieved. The chamber 20 is disposed under the arch and sole portions of the foot in the form illustrated. A resiliently compressible solid heel portion 24 is disposed rearwardly of the chamber. The chamber may advantageously be molded from a suitable material such as rubber or a synthetic resin.

Figure 2:
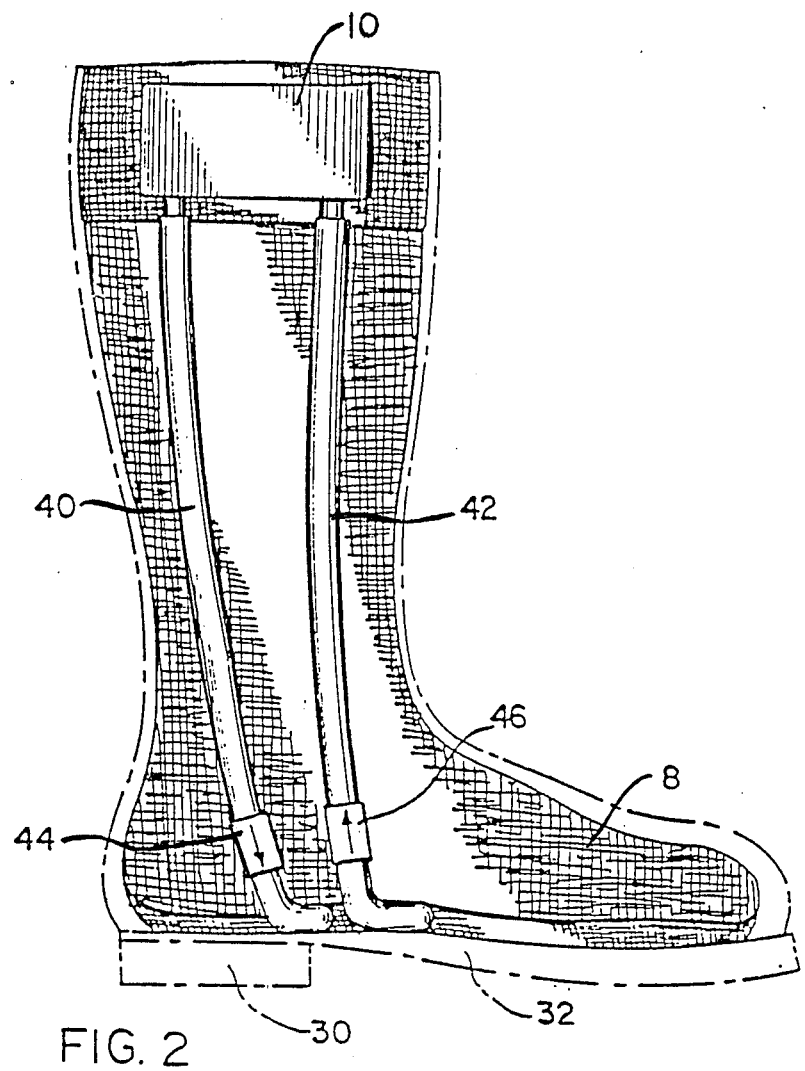
FIG. 2 is a partially broken away schematic elevational view of another side of the foot comforter apparatus of the present invention.
Figure 3:
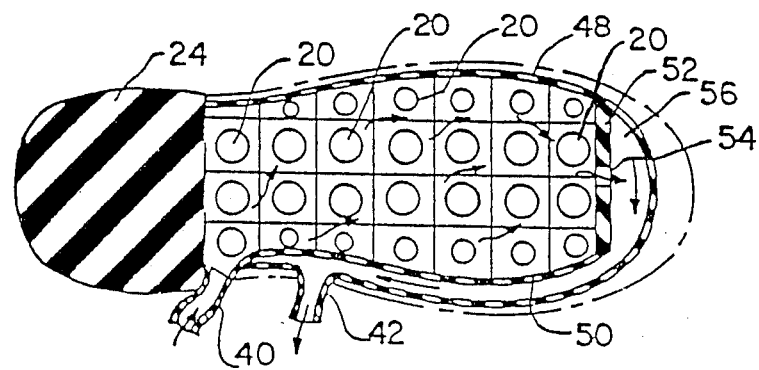
FIG. 3 is a cross-sectional illustration of the foot comforter apparatus of the present invention.

Referring to FIGS. 2 and 3, it is seen that a supply conduit 40, which may conveniently be a plastic tubular member, is in communication with a rear portion of the chamber. Fluid return conduit 42 is separated from the chamber by wall 50 and divider wall 52, the latter of which has passageway 54. Portion 56 of return conduit 42 is disposed forwardly of the chamber. It will be appreciated that by positioning the supply conduit 40 adjacent one end of the chamber and the return conduit 42 adjacent the other, directional flow from the rearward portion of the shoe to the forward portion is facilitated, although flow from the forward portion of the shoe to the rearward portion is also possible. Under known thermodynamic principles, having fluid flow generally the entire length of the longitudinal axis of chamber 20 will cause the maximum area of the foot to be warmed or cooled.

One of the unique aspects of the present invention is that an individual, by applying suitable pressure in a downwardly direction to the chamber which is shown uncompressed in FIG. 1, will overcome the resistance provided by resiliently compressible spaces 22 and will create a pumping action which causes air flow in the direction indicated by the arrow in FIG. 3. Release of pressure then causes replenishment of fluid in chamber 20 from conduit 40. As a result, normal walking action, or when desired, action intended solely for the purpose of creating a pumping action, such as by "marking time", will cause flow of fluid from chamber 20 to the heat exchanger, from which the fluid at elevated or reduced temperature will be returned to the chamber. While it will be appreciated that technically the chamber is defined by walls 48, 50, 52 in combination with heel 24 and upperwall 16 and lower wall 18, for convenience of reference herein, it will be described as being formed by the upper and lower walls 16, 18.

It will be appreciated that as heel 30 and sole 32 of boot 6 underlie chamber 20, application of force by the foot, particularly when the boot is resting on a solid surface, will serve to facilitate the pumping action.

Check valves 44 and 46 serve to resist flow in the reverse directions within conduits 40, 42. If desired, the arrangement of the check valves may be reversed so that fluid flow is from conduit 42, into portion 56, through chamber 20, and out conduit 40, where it then circulates through heat exchanger 10. Flow through chamber 20 would then be from generally the forward portion of the shoe to the rearward portion. In either design, the location of check valves 44 and 46 is important. As is well known under fluid mechanic theory, if they are located too far away from chamber 20, gas fluid would tend to compress in conduits 40 and 42 reducing the volume of gas circulated through heat exchanger 10.

In a preferred embodiment of the invention, air will serve as the fluid for the delivery of heat or cold to the foot. If desired, other fluids might be employed.

The heat exchanger may conveniently be composed of any suitable material, such as metal, plastic or the like and is preferably thermally insulated so as to minimize heat loss to the surrounding environment and body of the user.

In one embodiment, a heat exchanger conduit, which may have its ends connected respectively to the supply conduit 40 and return conduit 42, serves to provide a closed path of flow for fluid with the flow through the heat exchanger portion of the conduit permitting the heat exchanging effect to occur. Alternately, the heat exchanger ma be or have a sealed container to which the supply conduit 40 and return conduit 42 is connected externally through suitable tubular extension on the heat exchanger.

While for purposes of simplicity of disclosure reference has been made herein to heating or cooling action through the heat exchanger, it will be appreciated that for ventilation purposes, in instances where a change in temperature of the circulating fluid is not required, the source of heating or cooling may be omitted from the heat exchanger.

Figure 5:
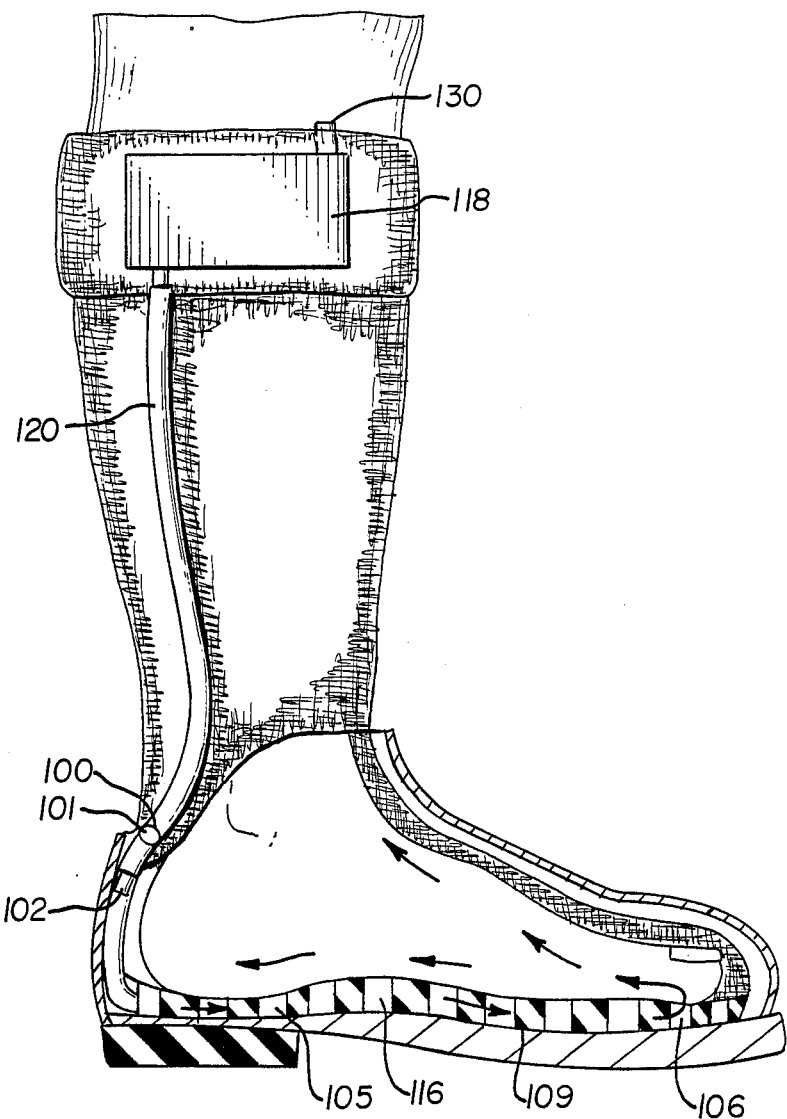
FIG. 5 is a partially schematic cross sectional illustration of the foot comforter apparatus of FIG. 4.
Figure 4:
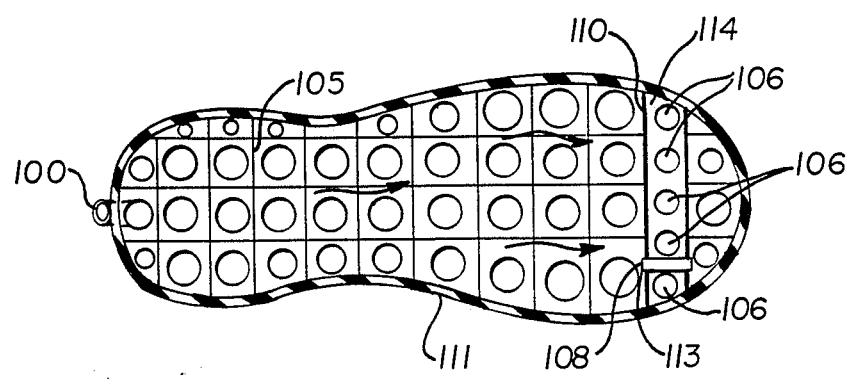
FIG. 4 is a top elevational view of a different embodiment of the foot comforter apparatus.

An alternative preferred embodiment is shown in FIGS. 4 and 5. In that embodiment, the foot comforter is designed to circulate air, which may be heated or cooled, around a person's foot rather than through a chamber below it. Although heat exchanger 118 is shown, its incorporation with the rest of the comforter is optional.

In the embodiment without heat exchanger 118 and connecting conduit 120, ambient air enters opening 100 which is positioned in the rearward portion of the shoe. Adjacent opening 100 is filter 101 which reduces the intake of foreign matter. Opening 100 and filter 101 are located in fluid supply conduit 104. Fluid supply conduit 104 also includes check valve 102 which allows ambient air to flow into conduit 104, but substantially blocks the flow of air from conduit 104 to the outside of the shoe. Chamber 105, which is defined by upper wall 107, lower wall 109, side wall 111, and divider wall 110 is in communication with intake conduit 104.

Check valve 108 is located in passageway 113 of divider wall 110. Discharge chamber 114 is formed by front wall 110, forward wall 112, upper wall 107, and lower wall 109. Upper wall 107 has formed in its surface a plurality of vent holes 106. Check valve 108 is designed to allow air to flow from chamber 105 into discharge chamber 114, but generally not from discharge chamber 114 to chamber 105. It may be appreciated that discharge chamber 114 may be made larger or smaller, if desired, or may be positioned at a different location relative to the forward and rearward portions of the shoe depending upon the specific application.

The pumping operation of the embodiment of FIGS. 4 and 5 is similar to that of FIGS. 1-3. As a person walks, he or she alternatively causes pressure to be placed on and released from upper wall 107. As pressure is placed on upper wall 107, spacers 116, which are preferably constructed like those of the embodiment of FIGS. 1-3, compress. That compression causes the volume of space within chamber 105 to reduce. The reduction in chamber volume forces air to flow through check valve 108 and into discharge chamber 114. Check valve 102 substantially prevents air from flowing out opening 100.

The additional air flowing into discharge chamber 114 causes air to be forced out through vent holes 106. When pressure is removed or reduced on upper wall 107, spacer members 116 then rapidly force upper and lower walls 107 and 109 apart, causing the volume of space within chamber 105 to increase. As the volume of chamber 105 increases, air is drawn from the outside through opening 100 into fluid supply conduit 104 and into chamber 105. Check valve 108 substantially prevents air from flowing from discharge chamber 114 to chamber 105. That cycle repeats over and over again as a person either walks or "marks time" causing the volume of chamber 105 to alternatively in crease and decrease, and air to be drawn through the system and out around a user's foot.

As an alternative, heat exchanger 118 may be connected through connecting conduit 120 to opening 100, although its inclusion is optional. The heat exchanger may be similar in construction to heat exchanger 10 of FIG. 2, except that ambient air would be drawn into its interior through opening 130 rather than air from fluid conduit 42. Suitable cooling material, such as ice or dry ice, or heating material, such as an electrical resistance heater or burning chemical, as described in the other preferred embodiment, may be disposed within the heat exchanger.

Air drawn through the heat exchanger would then be heated or cooled before it entered the foot comforter embodied in FIGS. 4 and 5. In this case, however, the heated or cooled air would not circulate in a closed circuit under a person's foot, but rather, would be expelled around a user's foot through discharge vents 106. This may be desirable in extreme heat or cold where heat conduction through upper wall 16 is insufficient.

Also, the embodiment of FIGS. 4 and 5 is particularly advantageous when it is desired to ventilate and heat or cool more of a person's entire foot than just the sole. A further advantage of circulating the air around the person's foot is that the air would aid in keeping the foot dry, thus reducing the risk of medical problems such as athlete's foot and other fungus. Also, circulating air through the shoe would tend to keep the leather or other shoe material drier, which would reduce the possibility of premature deterioration of the shoe itself.

It will be appreciated, therefore, that the present invention has provided a unique and effective means for creating a pumping action to either circulate a suitable fluid from foot warming or cooling position to heat exchanging positions or draw ambient air through the apparatus and discharge it generally around a user's foot.

Whereas particular embodiments of the invention have been described for purposes of illustration, it will be evident to those skilled in the art that numerous variations of the details may be made without departing from the invention as defined in the appended claims.

I claim:

1. Foot comforter apparatus comprising
   a foot supporting chamber having an upper wall and lower wall,
   said chamber being at least partially compressible to permit cyclic application of foot pressure to cause said chamber to act as a fluid pump, whereby application of pressure on said chamber will cause said chamber to at least partially compress and thereby discharge a portion of the fluid from said chamber and release of pressure from said chamber will cause said chamber to very rapidly expand, said expansion causing very rapid replenishment of fluid to said chamber,
   divider wall located at generally one end of the longitudinal axis of said chamber, said divider wall separating said chamber from an adjacent portion of said comforter for resisting the escape of fluid from said chamber,
   a front wall disposed forwardly of said divider wall for confinement of said air,
   said upper wall, said lower wall, said divider wall and said front wall forming a discharge portion,
   fluid supply conduit means for delivering fluid to said chamber, said fluid supply conduit means in communication with said chamber at generally the end of the longitudinal axis of said chamber opposite said divider wall,
   fluid return conduit means for delivering fluid from said chamber disposed between said fluid supply conduit means and said divider wall,
   valve means on said fluid supply conduit means and said fluid return conduit means for controlling the direction of fluid flow,
   passageway means through said divider wall, whereby said divider wall and passageway means will resist excessive flow rate of said fluid from said chamber to a portion of said comforter adjacent said chamber,
   said valve means, said divider wall and said passageway means cooperating to restrict the flow of fluid between the rearward portion of said chamber and said divider wall to substantially one direction along and parallel to the longitudinal axis of said chamber, and
   said fluid supply conduit means and said passageway means being in communication with relatively spaced portions of said chamber in order to facilitate said one direction fluid, whereby said fluid flow will be a closed circuit from said chamber through said divider wall into said passageway to said discharge portion and then to said fluid return conduit means and then into said fluid supply conduit means for returning to said chamber.

2. The apparatus of claim 1 including said one direction fluid flow being generally from the rearward portion of said chamber to said divider wall.

3. The apparatus of claim 2 including fluid receiver means in communication with said fluid supply conduit means for delivery of the fluid to said fluid supply conduit means.

4. The apparatus of claim 3 including said fluid receiver means being heat exchanger means.

5. The apparatus of claim 4 including said chamber being so sized and proportioned as to underlie only a portion of the user's foot.

6. The apparatus of claim 5 including resiliently compressible spacer means disposed intermediate said upper and lower walls, whereby compression of said chamber will effect movement of fluid from said chamber, through said passageway means, to said fluid return conduit and release of compression of said chamber will effect very rapid replenishment of fluid to said chamber from said fluid supply conduit means.

7. The apparatus of claim 6 including said spacer means comprising a plurality of individual column members.

8. The apparatus of claim 7 including heel support means disposed rearwardly of said chamber.

9. The apparatus of claim 8 including
first valve means within said fluid supply conduit means for resisting multi-directional fluid flow in said chamber, and
second valve means within said fluid return conduit means for resisting multi-directional fluid flow in said chamber.

10. The apparatus of claim 9 including said first valve means and said second valve means being check valves.

11. The apparatus of claim 10 including said heat exchanger means having electrically energized means for genera ting and transmitting heat to said fluid.

12. The apparatus of claim 10 including said heat exchanger means having chemically energized means for generating and transmitting heat to said fluid.

13. The apparatus of claim 10 including said heat exchanger means having a frozen material.

14. The apparatus of claim 8 including said conduit means being charged with air.

15. The apparatus of claim 1 including said fluid being air.

16. The apparatus of claim 15 including said one direction fluid flow being generally from the rearward portion of said chamber to said divider wall.

17. The apparatus of claim 16 including said upper wall having air vent means formed in its surface for discharging said air from said comforter.

18. The apparatus of claim 16 including said air vent means formed in the portion of said upper wall above said discharge chamber.

19. The apparatus of claim 18 including said chamber being so sized and proportioned as to underlie only a portion of the user's foot.

20. The apparatus of claim 19 including resiliently compressible spacer means disposed intermediate said upper and lower walls, whereby compression of said chamber will effect movement of said air from said chamber through said passageway means to said discharge chamber, and release of compression of said chamber will effect very rapid replenishment of said air to said chamber from said fluid supply conduit means.

21. The apparatus of claim 20 including said spacer means comprising a plurality of individual column members.

22. The apparatus of claim 21 including said first valve means and said second valve means including check valves.

23. The apparatus of claim 22 including fluid receiver means in communication with said fluid supply conduit means for delivery of said air to said fluid supply conduit means.

24. The apparatus of claim 23 including said fluid receiver means including heat exchanger means.

25. The apparatus of claim 24 including said heat exchanger means having electrically energized means for genera ting and transmitting heat to said air.

26. The apparatus of claim 24 including said heat exchanger means having chemically energized means for generating and transmitting heat to said air.

27. The apparatus of claim 24 including said heat exchanger means receiving ambient air and supplying it to said fluid supply conduit means.

28. The apparatus of claim 27 including said heat exchanger means altering the temperature of said ambient air.

* * * * *

UNITED STATES PATENT AND TRADEMARK OFFICE
CERTIFICATE OF CORRECTION

PATENT NO. : 4,800,867

DATED : January 31, 1989

INVENTOR(S) : ROBERT OWENS

It is certified that error appears in the above-identified patent and that said Letters Patent is hereby corrected as shown below:

Column 4, line 29, "ma" should be --may--.

Claim 1, column 6, line 51, --flow-- should be inserted after "fluid" (first occurrence).

Claim 11, column 7, line 28 "genera ting" should be --generating--.

Claim 25, column 8, line 32, "genera ting" should be --generating--.

Signed and Sealed this

Twenty-seventh Day of June, 1989

Attest:

DONALD J. QUIGG

Attesting Officer

Commissioner of Patents and Trademarks